United States Patent
Hansmann et al.

(10) Patent No.: US 12,161,813 B2
(45) Date of Patent: Dec. 10, 2024

(54) DEVICE FOR VENTILATING A PATIENT

(71) Applicant: Drägerwerk AG & Co. KGaA, Lübeck (DE)

(72) Inventors: Hans-Ullrich Hansmann, Barnitz (DE); Karsten Hiltawsky, Stockelsdorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1276 days.

(21) Appl. No.: 16/755,028

(22) PCT Filed: Oct. 1, 2018

(86) PCT No.: PCT/EP2018/076566
§ 371 (c)(1),
(2) Date: Apr. 9, 2020

(87) PCT Pub. No.: WO2019/072606
PCT Pub. Date: Apr. 18, 2019

(65) Prior Publication Data
US 2020/0316327 A1    Oct. 8, 2020

(30) Foreign Application Priority Data

Oct. 13, 2017    (DE) .................... 10 2017 009 603.1

(51) Int. Cl.
*A61M 16/20*    (2006.01)
*A61M 16/00*    (2006.01)
(Continued)

(52) U.S. Cl.
CPC ...... *A61M 16/205* (2014.02); *A61M 16/0003* (2014.02); *A61M 16/024* (2017.08);
(Continued)

(58) Field of Classification Search
CPC ............ A61M 16/205; A61M 16/0003; A61M 16/024; A61M 16/204; A61M 16/04;
(Continued)

(56) References Cited

U.S. PATENT DOCUMENTS 5,063,925 A    11/1991    Frank et al.
2006/0219245 A1*    10/2006    Holder .............. A61M 16/0666
                                                                128/205.24

(Continued)

FOREIGN PATENT DOCUMENTS

CN    101553268 A    10/2009
CN    103476332 A    12/2013
(Continued)

*Primary Examiner* — Joseph D. Boecker
*Assistant Examiner* — Maap Ahmed Ellabib
(74) *Attorney, Agent, or Firm* — McGlew and Tuttle, P.C.

(57) ABSTRACT

A patient module (20) is intended for use together with a pressure source (12). The patient module (20) couples the pressure source (12) for flow to a patient interface (14) that can be connected to the airways of a patient. The patient module (20) includes at least one valve device (30), which can be controlled by means of a piezo pump, which acts as a valve drive (34) and can preferably be operated at a high frequency. The at least one valve device (30) acts as an exhalation valve (28).

19 Claims, 8 Drawing Sheets

(51) Int. Cl.
*A61M 16/04* (2006.01)
*F04B 45/047* (2006.01)

(52) U.S. Cl.
CPC ......... *A61M 16/204* (2014.02); *F04B 45/047* (2013.01); *A61M 2016/0027* (2013.01); *A61M 2016/0033* (2013.01); *A61M 16/04* (2013.01); *A61M 2205/0294* (2013.01); *A61M 2205/07* (2013.01)

(58) Field of Classification Search
CPC .. A61M 2016/0027; A61M 2016/0033; A61M 2205/0294; A61M 2205/07; A61M 16/20; A61M 16/0833; A61M 2205/3592; A61M 16/206; F04B 45/047
See application file for complete search history.

(56) References Cited

U.S. PATENT DOCUMENTS

| | | | |
|---|---|---|---|
| 2013/0167843 A1* | 7/2013 | Kimm | A61M 16/209 128/205.24 |
| 2013/0186394 A1* | 7/2013 | Hallett | A61M 16/0057 128/205.24 |
| 2013/0331715 A1* | 12/2013 | Sano | G05D 7/005 251/331 |

FOREIGN PATENT DOCUMENTS

| | | |
|---|---|---|
| CN | 104870040 A | 8/2015 |
| DE | 112012001648 T5 | 1/2014 |
| DE | 102016009836 A1 | 2/2018 |
| JP | 2012086030 A | 5/2012 |
| WO | 2018033225 A1 | 2/2018 |

* cited by examiner

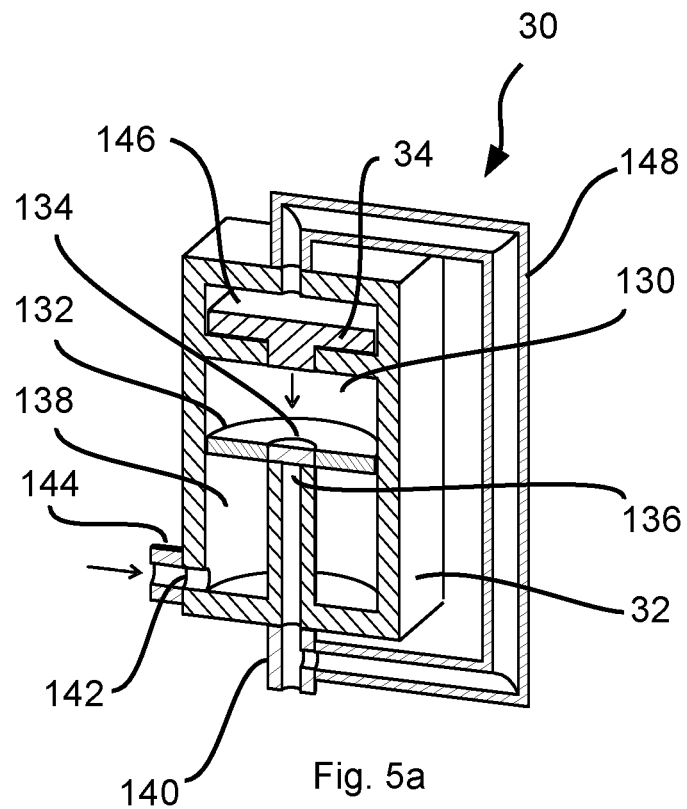
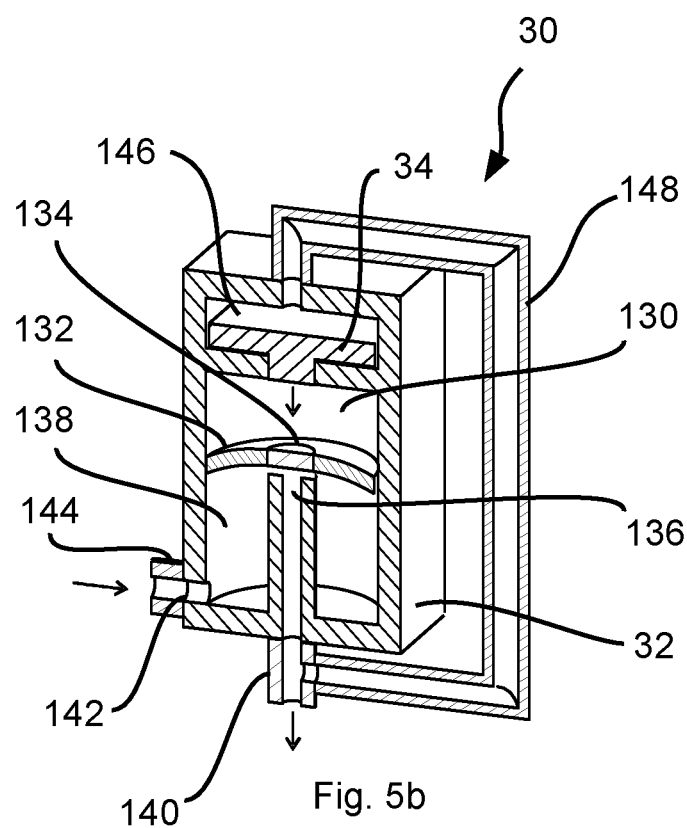

DEVICE FOR VENTILATING A PATIENT

CROSS REFERENCE TO RELATED APPLICATIONS

This application is a United States National Phase Application of International Application PCT/EP2018/076566, filed Oct. 1, 2018, and claims the benefit of priority under 35 U.S.C. § 119 of German Application 10 2017 009 603.1, filed Oct. 13, 2017, the entire contents of which are incorporated herein by reference.

TECHNICAL FIELD

The present invention pertains to a device, which is intended for use together with a pressure source, such as preferably a constant pressure source or a ventilator, and will hereinafter be called a patient module. A constant pressure source is, for example, a gas cylinder, a gas feed unit for providing a constant gas pressure or a gas supply unit, e.g., a wall-mounted supply unit in a hospital.

TECHNICAL BACKGROUND

For example, ventilators or anesthesia devices are known as devices for ventilating a patient. Ventilators and anesthesia devices—hereinafter called summarily ventilators or as ventilator in case of a single device, are used to provide breathing air for patients who are either completely unable to breathe independently or require assistance in breathing. The patients wear for this purpose, e.g., a face mask, which covers the mouth and the nose, or a tube, which is inserted into the mouth and the pharyngeal cavity of the patient. The face mask or the tube—hereinafter called summarily patient interface, are connected to the ventilator via at least one ventilation tube. The patient interface may also be a tracheal cannula.

SUMMARY

An object of the present invention is to propose a device that can be changed easily for ventilating a patient.

This object is accomplished according to the present invention by means of a device for ventilating a patient, which will hereinafter be called a patient module, is separated in space from a pressure source, especially from a ventilator acting as a pressure source, and is pneumatically connected to the pressure source.

Provisions are made for this purpose in such a patient module intended for use together with a pressure source for the patient module to couple the pressure source for flow with a patient interface, which is connected or can be connected to the airways of a patient and for the patient module to comprise at least one valve device acting as an exhalation valve. In case of two valve devices, one valve device acts as an exhalation valve and the other valve device as an inhalation valve.

The following provisions are made concerning the valve device or each valve device: The valve device or each valve device comprises a valve drive, a pressure chamber and a control pressure chamber. The valve drive is connected to the control pressure chamber in a fluid-communicating manner for generating a control pressure in the control pressure chamber and a piezo pump, which can preferably be operated at a high frequency and acts as a valve drive. The control pressure chamber is separated from the pressure chamber by means of a diaphragm element having a closing element. A first opening of the pressure chamber can be opened and closed by means of the closing element. The closing element, namely, a position of the closing element, can be controlled by means of the control pressure acting on the first diaphragm element.

The advantage of the concrete patient module is that important functional elements can be moved close to the patient, namely, into the patient module or at least into the area around the patient module, and that the patient module can be replaced with another patient module in a simple manner and without complications, for example, for cleaning purposes. The patient module may be coupled between the respective pressure source and a respective patient interface and forms a replaceable module, which can be detachably connected to the pressure source, on the one hand, and to the patient interface, on the other hand, in an active chain comprising the pressure source, the patient module and the patient interface.

Due to the patient module comprising at least one valve device acting as an exhalation valve, it is possible to use a very simple pressure source or constant pressure source, namely, for example, a compressed gas cylinder, which makes available a volume flow of breathing gas via a ventilation tube between the pressure source and the patient module and an overpressure relative to the ambient pressure. The ventilation of the patient can be carried out by means of this volume flow during the phase of inhalation in a manner basically known per se. A pressure curve during the phase of inhalation is controlled or regulated by the actuation of the exhalation valve. The exhalation valve is opened in a controlled or regulated manner, likewise in a manner basically known per se, for obtaining a pressure difference from the pressure in the patient's lungs, which difference is necessary for the exhalation, during a phase of exhalation following the phased of inhalation.

Advantageous embodiments of the present invention are the subject of the subclaims. References used here within the claims refer to the further configuration of the subject of the claim being referred to by the features of the respective dependent claims. They shall not be considered to represent abandonment of the wish to achieve an independent concrete protection for the features or combinations of features of a dependent claim. Furthermore, it shall be assumed in respect to an interpretation of the claims as well as of the description in case of a more specific concretization of a feature in a dependent claim that such a limitation is not present in the respective preceding claims as well as in a more general embodiment of the concrete patient module. Any reference in the description to aspects of dependent claims shall accordingly also expressly imply a description of optional features even without a special reference.

Provisions are made in one embodiment for the valve drive or each valve drive to comprise a piezo element, to which an electrical voltage can be applied, and for a pump diaphragm element of the valve drive to be able to be moved by means of the piezo element by a voltage-dependent change in the shape of the piezo element. The mobility of the pump diaphragm element is the basis of the function of the valve drive as a drive of the valve device. The valve drive replaces a hitherto necessary mechanical actuator inside the valve device. The valve device can be configured as a very small (miniaturized) unit due to the use of the piezo element and the pump diaphragm element can preferably be moved at a high frequency.

In a special embodiment of the patient module, the valve drive of the at least one valve device of the patient module can be arranged inside or outside the patient module. A compact, one-piece structural shape is obtained in case of a valve drive arranged inside the patient module. Replacement and a possible disposal of the patient module are possible and the valve drive remains preserved for a possible later use at another patient module in case of a valve drive arranged outside the patient module.

In one embodiment of the patient module, this has devices for detachable connection to the patient interface and/or devices for detachable connection to at least one ventilation tube coming from the pressure source.

The possibility of connecting the patient module to the patient interface and/or to the at least one ventilation tube coming from the pressure source in a detachable manner guarantees easy replaceability of a patient module with another patient module. Based on the possibility of the detachable connection, no technician is needed for such a replacement. Such a replacement can rather be carried out readily even by the hospital staff or even by the user of the patient module.

Severing and a later restoration of such a detachable connection is especially simple if a medical cone is used for this purpose. The ventilation tube or each ventilation tube is pulled off at the respective medical cone on an inlet side of the patient module for the replacement of the patient module and a new patient module is later attached to the inlet-side medical cone of a new patient module. The patient interface or a tube section leading to the patient interface is likewise detached on an outlet side of the patient module from the medical cone located there and is later attached to the outlet-side medical cone of the new patient module.

In a further, additional or alternative embodiment of the patient module, this has devices for detachable connection to at least one valve drive arranged outside the patient module. A tube between the valve drive and the other units of the valve device, which tube can be detached either from the valve drive or from the other units of the valve at at least one connection point, is an example of a device for the detachable connection of the at least one valve drive to the patient module, namely, to the units of the valve device that are located in the interior of the patient module.

In a special embodiment, the patient module comprises two valve devices with respective valve drives, which can be arranged inside or outside the patient module, wherein one of the at least two valve devices acts as an exhalation valve and one of the valve devices as an inhalation valve. A respective pressure and/or volume curve can be controlled and/or regulated during the phase of inhalation and the phase of exhalation, namely, by means of the patient module arranged close to the patient and the valve devices comprised by it in a patient module that comprises at least one valve device acting as an exhalation valve as well as as an inhalation valve.

Another embodiment of the patient module is characterized by a sensor mechanism comprised by the patient module as well as a control device, which may possibly also be arranged spaced apart from the patient module, wherein at least one control signal can be generated for actuating the at least one valve device by means of the control device on the basis of a sensor signal that can be obtained from the sensor mechanism. The advantage of the sensor mechanism comprised by the patient module and hence arranged close to the patient is above all that it delivers sensor signals that can be used especially well for an accurate actuation of the at least one valve device. The quality of the sensor signals is improved above all compared to sensor signals of a sensor mechanism in the area of a ventilator acting as a pressure source. A sensor signal of a sensor mechanism in or at the ventilator always represents a state that is already obsolete to a certain extent compared to a current state in the area of a breathing mask or the like based on the run time of the pneumatic conditions along the at least one ventilation tube to the ventilator. Moreover, the at least one ventilation tube leading to the ventilator acts as a low-pass filter, so that a sensor signal that can be obtained from a sensor mechanism in or at the ventilator is already reduced in terms of its dynamics.

A patient module, which comprises such a sensor mechanism and additionally at least one valve device acting as an exhalation valve or a valve device acting as an exhalation valve as well as a valve device acting as an inhalation valve, comprises the essential functional units for the ventilation of a patient, which were hitherto contained in a ventilator set up at a distance from the patient compared to the patient module.

The control device is separated in space from the patient module in a special embodiment of such a patient module and can be connected to the patient module in a communicating manner for receiving the at least one sensor signal from the sensor mechanism as well as for transmitting the at least one control signal to the at least one valve device of the patient module and is connected to this in a communicating manner during the operation of the patient module. The advantage of this embodiment is above all that the control device can also be preserved in case of a possible replacement of the patient module and is available for a later use with another patient module. The control device may definitely be arranged now at a distance from the patient compared to the patient module located close to the patient, so that the patient, who can carry the patient module, for example, on his body, does not have to likewise carry the control device on his body. Provisions may likewise be made for the control device to be able to be worn on the body as well. Provisions may likewise be made for the control device to be arranged in or at a ventilator acting as a pressure source or to be a part of the functionality of the ventilator. A special advantages arises in the latter case due to the fact that the ventilator acts now as an operating and user interface for the patient module and operating and/or display elements, which are present at the ventilator anyway, can also be used to operate, especially parametrize, the patient module, and that it is possible to check the function of the patient module by means of the ventilator acting as an operating and user interface for the patient module.

The patient module is operated automatically under the control of the control device. This control device comprises for this purpose in a manner known basically per se a processing unit in the form of or in the manner of a microprocessor as well as a memory. A control program, which can be executed by the processing unit and which is carried out during the operation of the patient module by the processing unit thereof, is or can be loaded into the memory. Operating actions of a user can be carried out either at the control device or at the ventilator acting now as an operating and user interface of the control device and of the patient module.

Insofar as the control program that can be executed by means of the control device and is executed during the operation of the patient module is concerned, the control device and the control program act as means for carrying out a process for operating the patient module. The present invention is thus also a computer program with program code instructions, which can be executed by a computer and are comprised by the control program, on the one hand, and, on the other hand, a storage medium with such a computer program, i.e., a computer program product with program code means, as well as finally also a control device, in the memory of which such a computer program is or can be loaded as means for carrying out the process for operating the patient module.

On the whole, the present invention is also a patient module system with a patient module as well as with a control device that can be arranged inside or outside the patient module, as they are respectively described here and below, wherein the patient module further comprises a sensor mechanism and wherein at least one control signal can be generated and is generated during the operation for ventilating the patient by means of the control device on the basis of at least one of the sensor signals that can be obtained from the sensor mechanism for actuating at least one valve device of the patient module. The control device may preferably be separated in space from the patient module. The control device is connected now to the patient module in a communicating manner for receiving the at least one sensor signal from the sensor mechanism as well as for transmitting the at least one control signal to at least one valve device of the patient module.

An exemplary embodiment of the present invention will be explained in more detail below on the basis of the drawings. Mutually corresponding subjects or elements are provided with the same reference numbers in all figures.

The exemplary embodiment shall not be considered to represent a limitation of the present invention. Variations and modifications are rather possible within the framework of the present disclosure, especially those variations and combinations that the person skilled in the art can find, with a view to accomplishing the object, for example, by combining or modifying individual features that are described in connection with the general or special part of the description and are contained in the claims and/or in the drawings and lead to a new subject due to the combinable features. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5a is a sectional view of an alternative embodiment of a valve device according to FIG. 3;

FIG. 5b is a sectional view of an alternative embodiment of a valve device according to FIG. 3;

DESCRIPTION OF PREFERRED EMBODIMENTS

Figure 1:
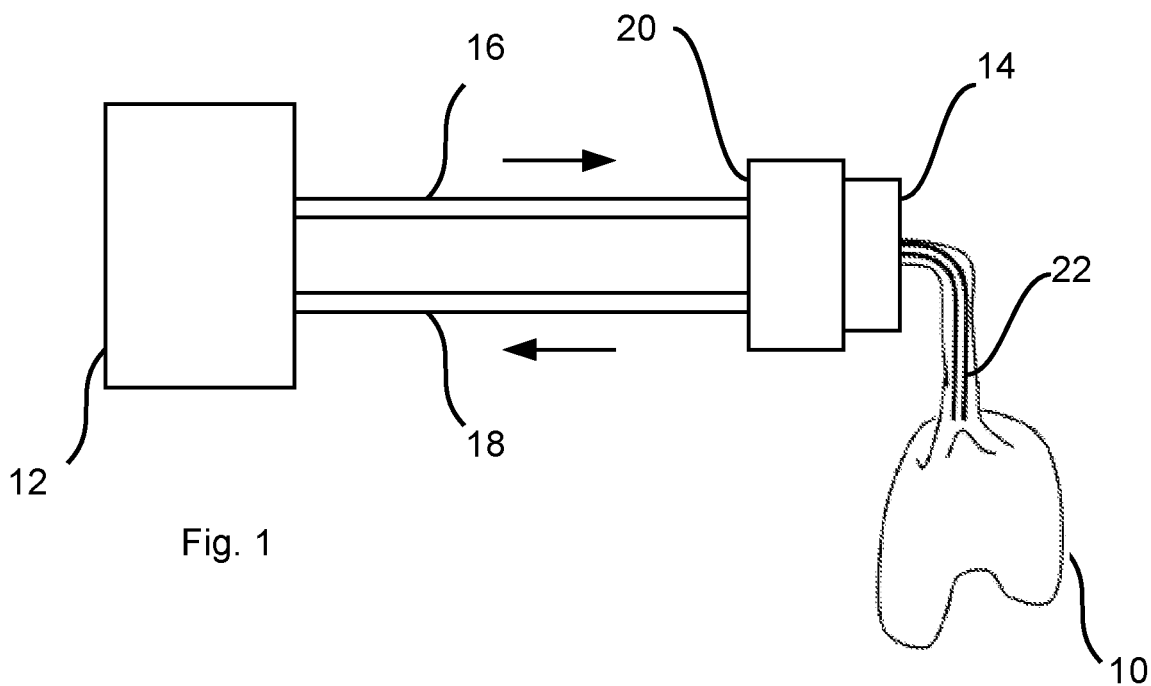
FIG. 1 is a schematic view showing the lungs of a patient, a pressure source intended for the ventilation of a patient and a patient module located close to the patient and a patient interface.

Referring to the drawings, the view in FIG. 1 shows, in a schematically highly simplified manner, the lungs of a patient (patient lungs 10) and a pressure source 12. The pressure source 12 is preferably a constant pressure source, for example, a gas cylinder, a gas feed unit for supplying a constant gas pressure or a gas supply unit. A medical device intended for ventilating the patient, especially a medical device in the form of a ventilator with a pressure source 12 or of a ventilator with a pressure source in the form of a combined anesthesia device and ventilator, preferably acts as a pressure source 12. A pressurized gas cylinder, a compressor, especially a radial compressor, or a wall outlet of a medical compressed air system, for example, in a hospital, may be considered for use as a pressure source as well. The pressure source 12 may consequently be preferably a constant pressure source in the form of a pressurized gas cylinder, a compressor, especially a radial compressor, or a wall outlet of a medical compressed air system, for example, in a hospital.

The pressure source 12 is indirectly connected to the airways of the patient and the patient's lungs 10 by means of a coupling piece hereinafter called patient interface 14 as well as by means of at least one ventilation tube 16, 18, namely, of an inhalation tube 16 or by means of an inhalation tube 16 and an exhalation tube 18. The arrows above the inhalation tube 16 and under the exhalation tube 18 illustrate the direction of the volume flow, which direction results during the operation. Instead of an exhalation tube 18 connected to the pressure source 12, said exhalation tube may also be open on one side to the environment, for example, in the form of a short tube section.

A patient module 20, to which the at least one ventilation tube 16, 18 is connected, is located close to the patient and is, for example, carried by the patient himself. The patient module 20 optionally comprises internally a so-called Y-piece, with which the inhalation branch and the exhalation branch are merged in a manner basically known per se, and are led in the merged form to the patient interface. Without such a Y-piece, the patient module 20 and a housing itself, surrounding the patient module 20, act as means for merging the inhalation branch and the exhalation branch to the patient interface 14.

The patient interface 14 may be a so-called face mask or the like, which is intended for ventilating a patient. Moreover, the patient interface 14 may also be a so-called tube 22 (endotracheal tube) or an endotracheal cannula. The abovementioned Y-piece may be located in or at the patient module 20 or be a part of the patient interface 14.

Figure 2:
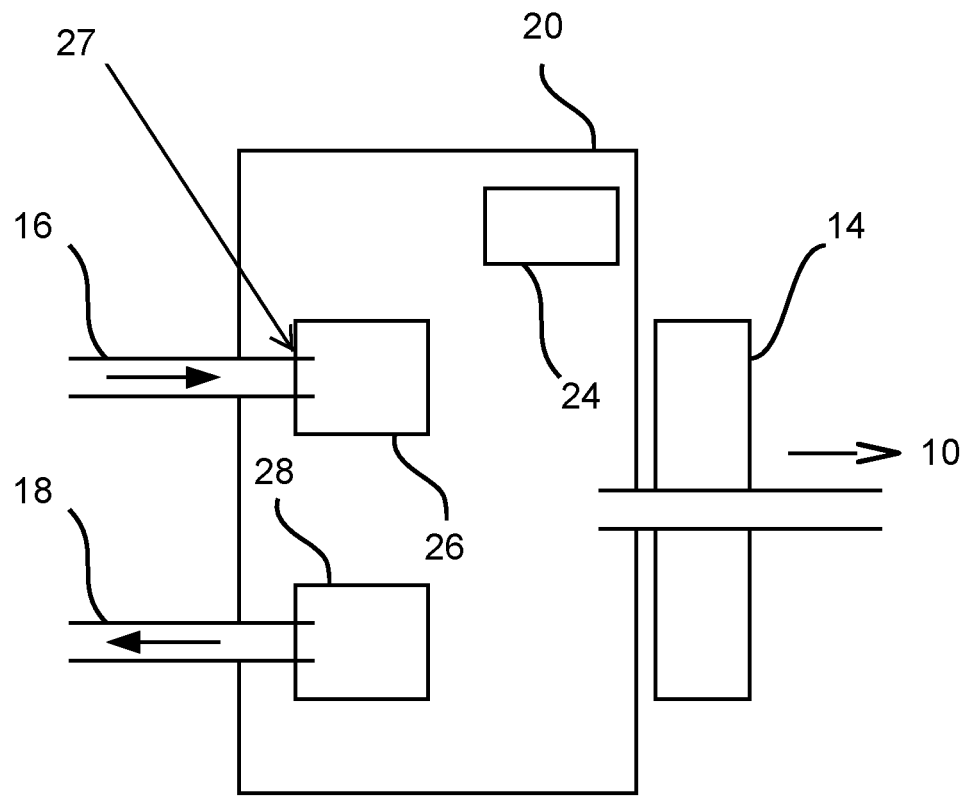
FIG. 2 is a schematic view showing the patient module with further details, namely, at least one valve device comprised by the patient module.

The view in FIG. 2 shows, likewise in a schematically highly simplified manner, an embodiment of the patient module 20 with further details. Accordingly, the patient module 20 comprises a sensor mechanism 24, which may possibly also be a distributed sensor mechanism, and which comprises at least one sensor, for example, a pressure sensor and/or a flow sensor. Furthermore, a valve 26, 28 each (inhalation valve 26, exhalation valve 28) are associated with the end of the inhalation tube 16 and with the end of the exhalation tube 18 in the patient module 20 in the embodiment shown. The two valves 26, 28 preferably have an identical or at least similar configuration, and the views discussed below pertain to possible embodiments of these valves 26, 28. The inhalation valve 26 is, in principle, optional. In an embodiment without inhalation valve 26, the inhalation pressure and its change during the phase of inhalation is set by an actuation of the exhalation valve 28 and, for example, the patient module 20 is opened towards the environment in a more or less controlled manner for obtaining the desired pressure curve. The patient module 20 includes a pressure source coupling 27 to couple the patient module to the pressure source 12.

Figure 3A:
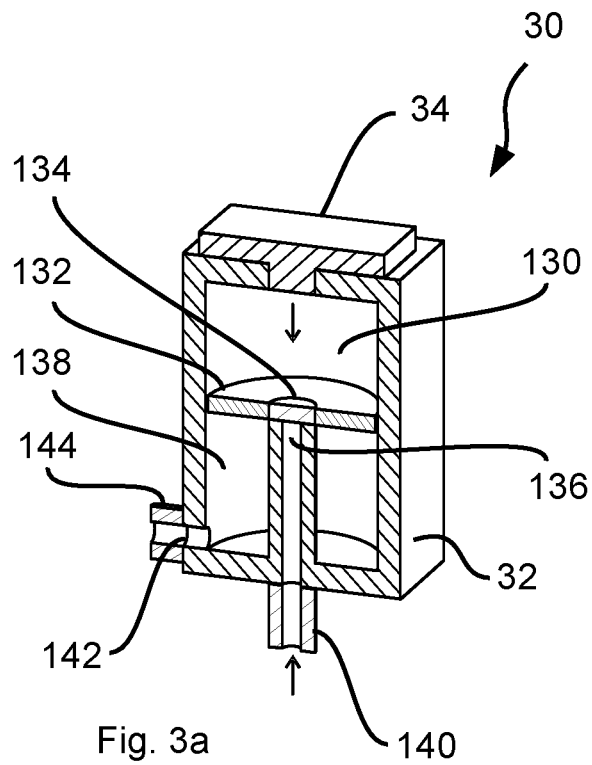
FIG. 3a is a sectional view of an embodiment of a valve device comprised by the patient module.
Figure 3B:
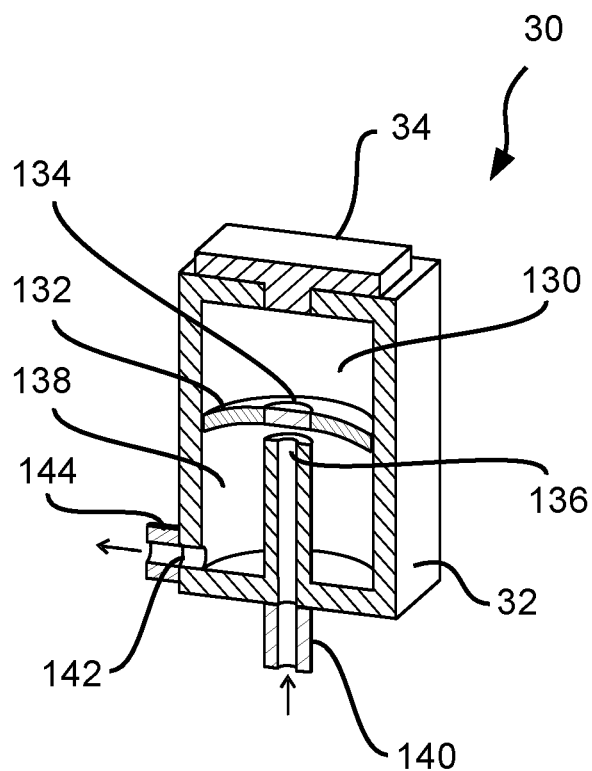
FIG. 3b is a sectional view of an embodiment of a valve device comprised by the patient module.
Figure 5C:
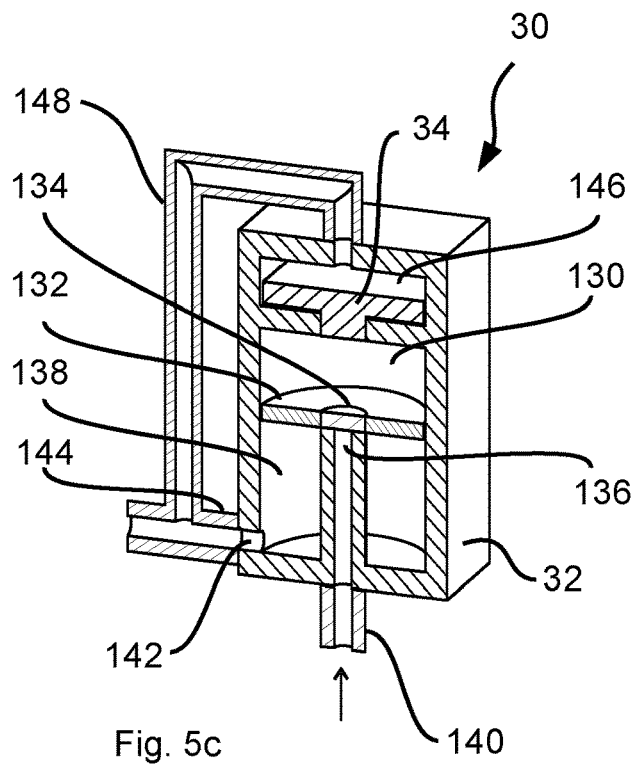
FIG. 5c is a sectional view of an alternative embodiment of a valve device according to FIG. 3.
Figure 5D:
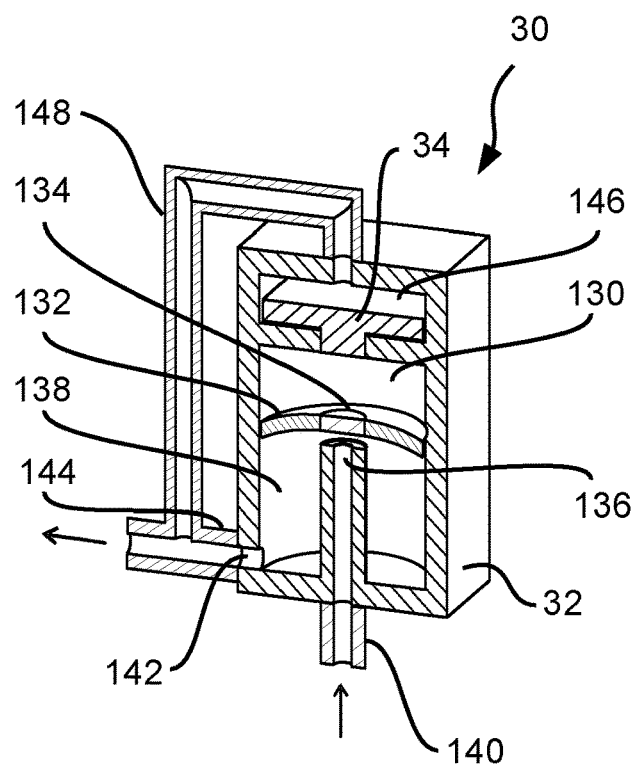
FIG. 5d is a sectional view of an alternative embodiment of a valve device according to FIG. 3.

The views in FIG. 3 (FIGS. 3a, 3b) and FIG. 5 (FIGS. 5a through 5d) show a valve device 30 acting as a pneumatic control device. The valve device 30 according to FIG. 3 is considered for use as an inhalation valve 26 and as an exhalation valve 28. The valve device 30 according to FIG. 5 is likewise considered for use as an inhalation valve 26. Each valve device 30 comprises a housing 32 and a pumping device connected to the housing 32 and acting as a valve drive 34. A piezo pump is used as a pumping device/valve drive 34. Flow is preferably possible in two directions through the pumping device/the piezo pump and the pumping device/the piezo pump is consequently a two-way pump.

A valve device 30 may have more than one valve drive 34 (pumping device/piezo pump). The piezo pumps may be configured as a stack of piezo pumps connected in series. The pump pressures of a plurality of piezo pumps can be combined by means of the stacking. As an alternative, a plurality of piezo pumps connected in parallel may be present in the valve device 30.

Figure 4A:
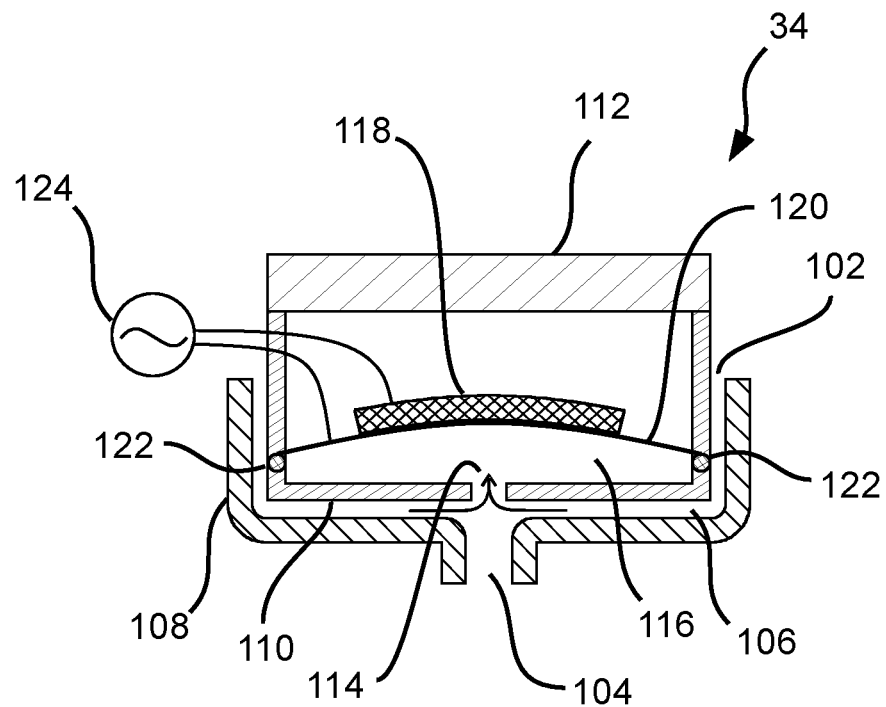
FIG. 4a is a sectional view of an embodiment of a valve drive of a valve device.
Figure 4B:
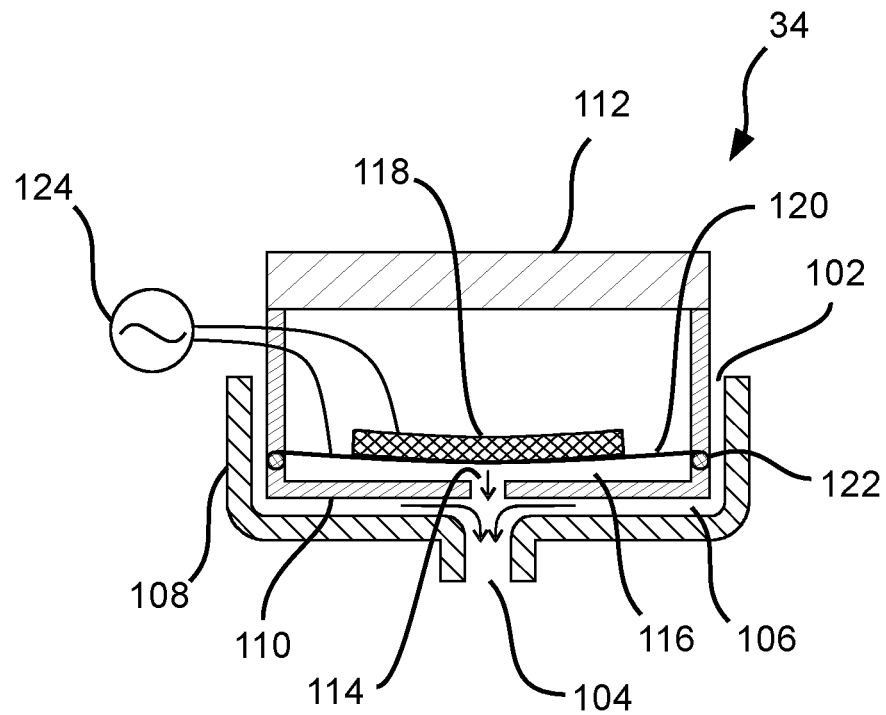
FIG. 4b is a sectional view of an embodiment of a valve drive of a valve device.

FIG. 4 (FIGS. 4a, 4b) shows the valve drive 34 with further details. Accordingly, the valve drive 34 has a first two-way passage opening 102 and a second two-way passage opening 104, which are connected by a two-way duct 106. The two-way duct 106 extends between an outer housing 108 and an inner housing 110. The second two-way passage opening 104 is formed in the outer housing 108. The first two-way passage opening 102 is obtained because of a distance between an edge of the outer housing 108 and the adjoining inner housing 110. The inner housing 110 is closed by means of a cover plate 112.

A pumping opening 114, which connects the two-way duct 106 to a pump chamber 116, is arranged in the two-way duct 106. A piezo element 118 and a pump diaphragm element 120 are arranged in the pump chamber 116. The pump diaphragm element 120 is connected to the piezo element 118, on the one hand, and to the inner housing 110 via the connection element 122, on the other hand. Alternating electrical voltages are applied to the piezo element 118 by means of an alternating voltage generator 124 in a manner basically known per se. These cause a voltage-induced deformation of the piezo element 118, and this deformation leads to a controlled vibration of the pump diaphragm element 120. Based on an alternating voltage, which is sent by means of the alternating voltage generator 124 and which is preferably a high-frequency voltage, the pump diaphragm element 120 vibrates in the pump chamber 116 at a corresponding, preferably high frequency, and pumping shocks are generated as a result by the resulting change in the volume of the pump chamber 116 (function of the piezo pump acting as a valve drive 34, preferably as a high-frequency pump). These pumping shocks may act into the two-way duct 106 due to the pumping opening 114 and bring about a flow of a respective fluid, for example, air, through the two-way passage opening 104.

The flow through the pumping opening 114, which is directed out of the pump chamber 116, is directed to the second two-way passage opening 104, i.e., a pumping shock, which is generated by a reduction of the volume of the pump chamber 116, is directed by the pumping opening 114 directly to the second two-way passage opening 104. The flow between the pumping opening 114 and the second two-way passage opening 104 carries along in this case the fluid in the two-way duct 106, so that a flow from the first two-way passage opening 102 to the second two-way passage opening 104 is generated. The fluid is sucked from the two-way duct 106 through the pumping opening 114 into the pump chamber 116 during an increase in the volume of the pump chamber 116. The fluid is sucked in this case from the two-way duct 106 into the pump chamber 116.

The pumping opening 114 is arranged now at such a distance from the second two-way passage opening 104 that only a small percentage of fluid flows through the second two-way passage opening 104 into the two-way duct 106 through the pumping opening 114 into the pump chamber 116. The larger portion of the fluid is sucked into the pump chamber 116 from the first two-way passage opening 102 through the two-way duct 106 and the pumping opening 114. When the valve drive (piezo pump) 34 is switched off, there is no directed flow in the two-way duct 106. There rather is a free flow path now through the two-way duct 106 between the first two-way passage opening 102 and the second two-way passage opening 104, and this free flow path may be directed in both directions. A pressure equalization can thus take place between the first two-way passage opening 102 and the second two-way passage opening 104. No relief valve or the like is therefore needed.

In the embodiment of the valve device 30 according to FIG. 3a, the valve drive 34 is configured and arranged to pump air from the environment into a control pressure chamber 130 in the interior of the housing 32 of the valve device 30. Consequently, a pressure increase is generated in the control pressure chamber 130 by means of the valve drive 34. The arrow pointing vertically downwards under the valve drive 34 shows the control flow direction, with which the fluid flow away from the valve drive 34 (out of the piezo pump) is shown. The valve drive 34 is connected to the control pressure chamber 130 in a fluid-communicating manner for generating a control pressure in the control pressure chamber 130.

Together with a closing element 134, a diaphragm element 132 forms an elastically movable wall of the control pressure chamber 130. The diaphragm element 132 is connected, furthermore, to the closing element 134, especially in one piece with the closing element 134. The closing element 134 is configured to close or to open a first opening 136 of a pressure chamber 138 formed in the interior of the housing 32. The diaphragm element 132 and the closing element 134 may preferably be connected to one another in one piece. The diaphragm element 132 and the closing element 134 divide the interior of the housing 32 of the valve device 30 and separate the control pressure chamber 130 from the pressure chamber 138. The first opening 136 may have a diameter of 1 mm to 10 mm. The selected diameter of the first opening 136 depends on the admission pressure with which the pneumatic valve device 30 operates.

The diaphragm element 132 is deflected to the opening 136 in the situation shown in FIG. 3a on the basis of an increased pressure in the control pressure chamber 130. The closing element 134 is pressed now onto the first opening 136 and the first opening 136 is closed. The diaphragm element 132 is deflected in the opposite direction and the first opening 136 is open in the situation shown in FIG. 3b.

When the valve device 30 according to FIG. 3 acts as an inhalation valve 26 in a patient module 20 (FIG. 2), the pressure source 12 (FIG. 1) is connected, for example, to a first connection line element 140, at the end of which the first opening 136 is located in the interior of the housing 32 (FIG. 1). The volume flow resulting from such a pressure source is represented by the vertically upwards pointing arrow shown under the connection line element 140, which indicates the flow direction in the pump. The pressure generated by the pressure source at the first opening 136 is not possibly sufficient to compensate the pressure generated by means of the valve drive 34 in the control pressure chamber 130. The closing element 134 correspondingly closes the opening 136 until a control pressure, whose force acting on the diaphragm element 132 is weaker than the force that acts on the diaphragm element 132 based on the pressure source, is generated in the control pressure chamber 130 by means of the valve drive 34.

The pressure chamber 138 further has a second opening 142, which is joined by a second connection line element 144. The second connection line element 144 may be connected to additional pneumatic components or be an outlet to a patient or to the patient interface 14 (FIG. 1)—in case of an action as an inhalation valve 26—or to the environment—in case of an action as an exhalation valve. As long as the closing element 134 closes the first opening 136, no fluid flows through the second opening 142.

The view in FIG. 3b shows a situation as it arises in the case of a switched-off valve drive 34. The valve drive 34 (the piezo pump) forms here an open fluid-communicating connection between the control pressure chamber 130 and the environment, i.e., pressure equalization takes place between the control pressure chamber 130 and the environment, so that ambient pressure is present in the control pressure chamber 130. The pressure in the first connection line element 140 is now higher—for example, due to a connected pressure source 12 (FIG. 1)—than the pressure in the control pressure chamber 130, which acts on the diaphragm element 132. The diaphragm element 132 is pressed therefore with the closing element 134 into the control pressure chamber 130, so that the closing element 134 opens the first opening 136. The first opening 136 and the second opening 142 are then connected to one another in a fluid-communicating manner via the pressure chamber 138, so that a fluid can flow from the first opening 136 to the second opening 142 (and from the first connection line element 140 into the second connection line element 144). The resulting volume flow is illustrated by the arrow shown next to the second connection line element 144, which indicates the flow direction. The pneumatic valve device 30 is opened now.

The pneumatic valve device 30 according to FIG. 3 (FIGS. 3a, 3b) and FIG. 5 (FIGS. 5a, 5b; FIGS. 5c, 5d) may act as a proportional valve. The distance between the closing element 134 and the first opening 136 can be controlled depending on how intensely the valve drive 34 pumps, i.e., on how high the pressure is in the control pressure chamber 130. Only a small fluid flow can flow from the first opening 136 to the second opening 142 in case of short distances. A larger fluid flow can flow between the first opening 136 and the second opening 142 in case of a great distance, i.e., in case of a low control pressure. In case of an action as a proportional valve, the pressure drag is kept at a constant value at the first opening 136.

The views in FIG. 5 (FIGS. 5a, 5b as well as FIG. 5c, 5d) show a special embodiment of the valve device 30 according to FIG. 3. This valve device 30 may be used as an inhalation valve 26 in the patient module 20 (FIG. 2) and is controlled as a function of the back pressure. The back pressure is the pressure that becomes established in a fluid flowing out of the pneumatic valve device 30. The admission pressure is correspondingly the pressure that becomes established during the flow into the pneumatic valve device 30. When—as is shown in FIG. 5b—the fluid flows from the second opening 142 to the first opening 136 with the closing element 134 opened, the admission pressure state is present at the second opening 142 and the pressure chamber 138 connected to the second opening 142. The back pressure is consequently present at the first opening 136 and at the first connection line element 140 connected to it.

The embodiments according to FIG. 5 comprise first the same elements as the embodiment according to FIG. 3, so that reference is made to the description given there. A flow direction that is reversed compared to the flow direction through the valve device 30 according to FIG. 3 is provided concerning the flow direction through the valve device 30 according to FIGS. 5a, 5b. Accordingly, a pressure source, for example, a pressure source 12 (FIG. 1) may have been connected or may be connected at the second connection line element 144 and a patient interface 14 (FIG. 1) may have been connected or may be connected at least indirectly at the first connection line element 140.

In addition to the embodiment according to FIG. 3, the embodiment according to FIG. 5 comprises a connection chamber 146 belonging to the valve drive 34 and a branch line element 148 acting as a branch or connection line. A fluid is removed from the connection chamber 146 during the operation of the valve device 30 during a pumping operation and is pumped into the control pressure chamber 130 by means of the valve drive (piezo pump) 34.

Further, the connection chamber 146 is connected to the first connection line element 140 via the branch line element 148 in a fluid-communicating manner. A pressure equalization can thus take place between the first connection line element 140 as well as the first opening 136 and the connection chamber 146 via the branch line element 148. The back pressure is consequently present in the connection chamber 146.

When and as long as the valve drive 34 is switched on, a higher pressure is present in the control pressure chamber 130 than in the pressure chamber 138 and at the first opening 136. The diaphragm element 132 is pressed therefore with the closing element 134 onto the first opening 136 and it closes the first opening 136. A volume flow from the (inlet-side) second opening 142 to the (outlet-side) first opening 136 is not possible and a possible previous volume flow is interrupted.

As soon as the valve drive 34 is switched off, an open fluid-communicating connection becomes established (via the two-way duct 106; FIG. 3) between the control pressure chamber 130 and the connection chamber 146. A pressure equalization can thus take place between the connection chamber 146 and the control pressure chamber 130, so that the back pressure becomes established in the control pressure chamber 130. The same pressure is thus present in the control pressure chamber 130 as at the first opening 136 and as at the first connection line element 140.

Since the admission pressure in the pressure chamber 138 is higher than the back pressure because of the pressure source connected at the second connection line element 144, the diaphragm element 132 is pushed with the closing element 134 into the control pressure chamber 130 (away from the first opening 136). The closing element 134 is thus brought into the open state, so that the first opening 136 is opened. A fluid can thus flow between the (inlet-side) second opening 142 and the (outlet-side) first opening 136. In case of an action as an inhalation valve 26 in a patient module 20 according to FIG. 2, the pressure source 12 is connected to the second connection line element 144 leading to the second opening 142 and the first connection line element 140 joining the first opening 136 is open, for example, towards the interior of the patient module 20 and hence indirectly to the patient interface 14 and to the airways of the patient or is connected to the patient interface 14.

FIG. 5b shows an operating state of the valve device 30, in which the valve drive 34 generates a pressure that generates in the control pressure chamber 130, together with the back pressure, a pressure that causes the diaphragm element 132 and the closing element 134 to be deflected away from the first opening 136, so that a volume flow from the second opening 142 to the first opening 136 is possible. The actuation of the valve device 30 consequently takes place in a back pressure-dependent manner.

The valve device 30 according to FIGS. 5a, 5b thus represents a back pressure-controlled pressure drag (the valve device 30 is a back pressure-controlled pressure drag/acts as a back pressure-controlled pressure drag). The opening state of the closing element 134 and the distance between the closing element 134 and the first opening 136 are controlled as a function of the back pressure during the operation of the valve device 30. Depending on the value of the back pressure, the valve drive (piezo pump) 34 can pump now only a certain volume into the control pressure chamber 130. When a lower back pressure is present, the control pressure will also be lower in the control pressure chamber 130 than if a higher back pressure were present. The distance between the closing element 134 and the first opening 136 is thus increased at a lower back pressure, because the diaphragm element 132 is pushed more deeply into the control pressure chamber 130 by the lower control pressure that results from the lower back pressure than in case of a higher back pressure.

The views in FIGS. 5c, 5d show another back pressure-controlled embodiment of the valve device 30. Contrary to the embodiment according to FIGS. 5a, 5b, a pressure source, for example, a pressure source 12 (FIG. 1), is or can be connected to this valve device 30 at the first connection line element 140, and a patient interface 14 (FIG. 1) is or can be connected at the second connection line element 144. Accordingly, the first connection line element 140 acts in this embodiment as an inlet and the second connection line element 144 as an outlet, as this is also indicated by the two arrows in the view in FIG. 5d. A volume flow is possible in the situation shown in FIG. 5d through the valve device 30 from the (inlet-side) first connection line element 140 to the (outlet-side) second connection line element 144 and a back pressure control also takes place in this case by means of the patient-side (outlet-side) pressure.

Figure 6:
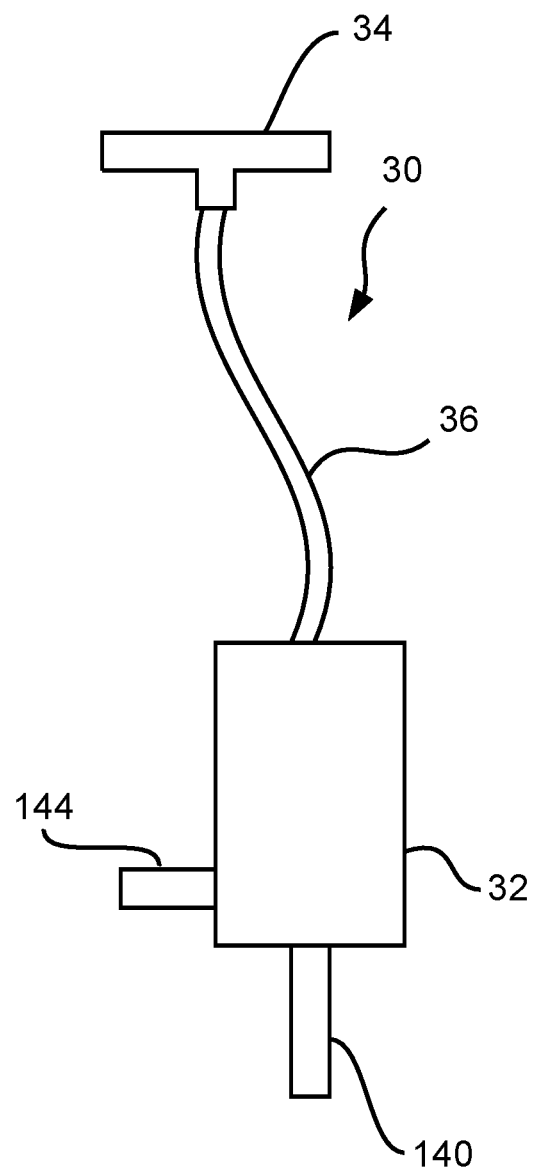
FIG. 6 is a schematic view of another alternative embodiment of a valve device according to FIG. 3 with a valve drive that can be arranged at a spaced location in space from the other elements of the valve device.

It applies to all the valve devices 30 shown (FIG. 3, FIG. 5) that the valve drive 34 is located either—as is shown—inside the housing 32 of the valve device 30 or, as an alternative, it may also be placed outside the housing 32 and hence separated in space from the rest of the components of the valve device 30. As this is shown in FIG. 6 on the basis of the view in FIG. 3a and in a schematically highly simplified form—the valve drive 34 is connected by means of a connection in the form of a tube 36 or the like to the housing 32 of the valve device 30 and the valve drive 34 is coupled with the control pressure chamber 130. The valve drive 34 is connected to the control pressure chamber 130 in a fluid-communicating manner for generating a control pressure in the control pressure chamber 130 in this case as well. This correspondingly applies to the embodiments according to FIG. 5, in which case the valve drive 34 is arranged in a separate housing (not shown), whose interior acts as a connection chamber 146, and wherein the branch line element 148 opens, for example, in the form of another tube or the like, into the connection chamber 146 on one side.

FIG. 7 (FIGS. 7a through 7e) shows the diaphragm element 132 and the closing element 134. For the sake of greater clarity, the reference numbers are shown only in the view in FIG. 7a. The diaphragm element 132 and the closing element 134 are located in the interior of the housing 32 of the valve device 30 and separate the control pressure chamber 130 from the pressure chamber 138.

Figure 7A:
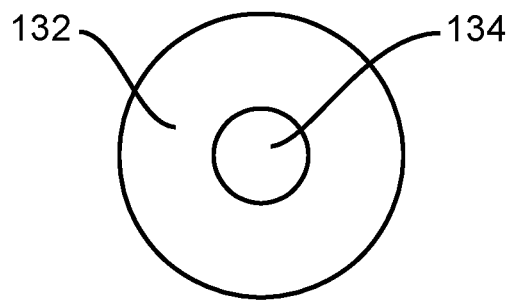
FIG. 7a is a schematic view of a diaphragm element and a closing element associated with the diaphragm element showing pressures acting on the different sides (underside or top side) and sections (diaphragm element or closing element)
Figure 7B:
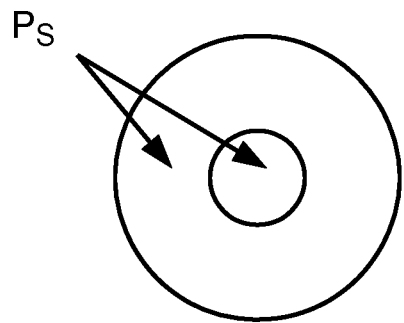
FIG. 7b is a schematic view of a diaphragm element and a closing element associated with the diaphragm element showing pressures acting on the different sides (underside or top side) and sections (diaphragm element or closing element)
Figure 7C:
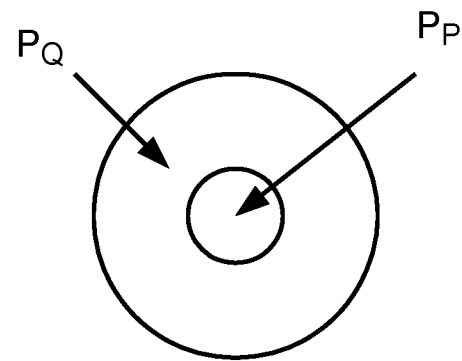
FIG. 7c is a schematic view of a diaphragm element and a closing element associated with the diaphragm element showing pressures acting on the different sides (underside or top side) and sections (diaphragm element or closing element)

The view in FIG. 7b shows the control pressure chamber-side (control pressure chamber 130) surface of the diaphragm element 132 (outside) and the closing element 134 (inside) of the valve device 30 in FIGS. 5a, 5b. The control pressure $P_S$ from the control pressure chamber 130 is present here both in an outer area, i.e., at the closing element 134, as well as in an inner area, i.e., at the closing element 134. The view in FIG. 7c shows the other, i.e., the pressure chamber-side (pressure chamber 138) surface of the diaphragm element 132 and of the closing element 134 of the valve device 30 in FIGS. 5a, 5b. The pressure $P_Q$ of the pressure source connected to the second connection line element 144 is present on this side of the surface in the outer area, i.e., at the diaphragm element 132, and the patient-side pressure $P_P$ is present in the inner area, i.e., at the closing element 134.

Figure 7D:
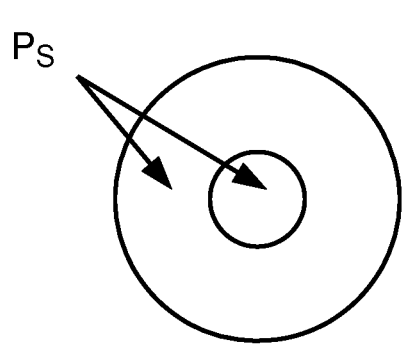
FIG. 7d is a schematic view of a diaphragm element and a closing element associated with the diaphragm element showing pressures acting on the different sides (underside or top side) and sections (diaphragm element or closing element)
Figure 7E:
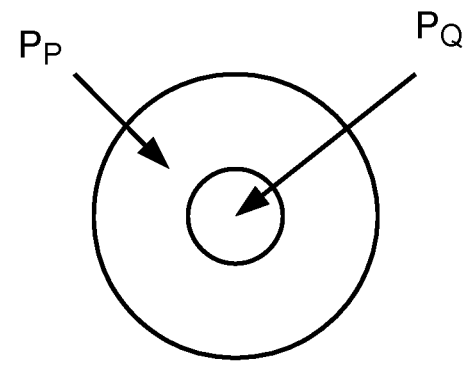
FIG. 7e is a schematic view of a diaphragm element and a closing element associated with the diaphragm element showing pressures acting on the different sides (underside or top side) and sections (diaphragm element or closing element)

The view in FIG. 7d shows the control pressure chamber-side surface of the diaphragm element 132 and of the closing element 134 of the valve device 30 in FIGS. 5c and 5d. The control pressure $P_S$ from the control pressure chamber 130 is present here both in an outer area, i.e., at the diaphragm element 132, and in an inner area, i.e., at the closing element 134. The view in FIG. 7e shows the pressure chamber-side surface of the diaphragm element 132 and of the closing element 134 of the valve device 30 in FIG. 5c, 5d. The patient-side pressure $P_P$ is present on this side of the surface in the outer area, i.e., at the diaphragm element 132, and the pressure $P_Q$ of the pressure source connected to the second connection line element 144 is present in the inner area, i.e., at the closing element 134.

In a patient module 20 according to FIG. 2, this comprises two valve devices 30, namely, a first valve device 30 acting as an inhalation valve 26 and a second valve device 30 acting as an exhalation valve 28, the respective corresponding valve drive 34 being arranged either likewise in the interior of the patient module 20 or also outside the patient module 20.

In a valve device 30 according to FIG. 3, which acts as an inhalation valve 26, the inhalation tube 16 coming from the pressure source 12 is connected to the first connection line element 140 and the second connection line element 144 is open towards the interior of the patient module 20 or is connected to the patient interface 14. In the case of a valve device 30 according to FIG. 3, which acts as an exhalation valve 28, the exhalation tube 18, which leads to the pressure source 12 or is open towards the environment, is connected to the second connection line element 144, and the first connection line element 140 is open towards the interior of the patient module 20 or is connected to the patient interface 14.

The patient module 20 minimally comprises exactly one valve device 30, namely, a valve device 30 acting as an exhalation valve 28, with a valve drive 34 arranged either in the interior of the patient module 20 or outside the patient module 20.

Figure 8:
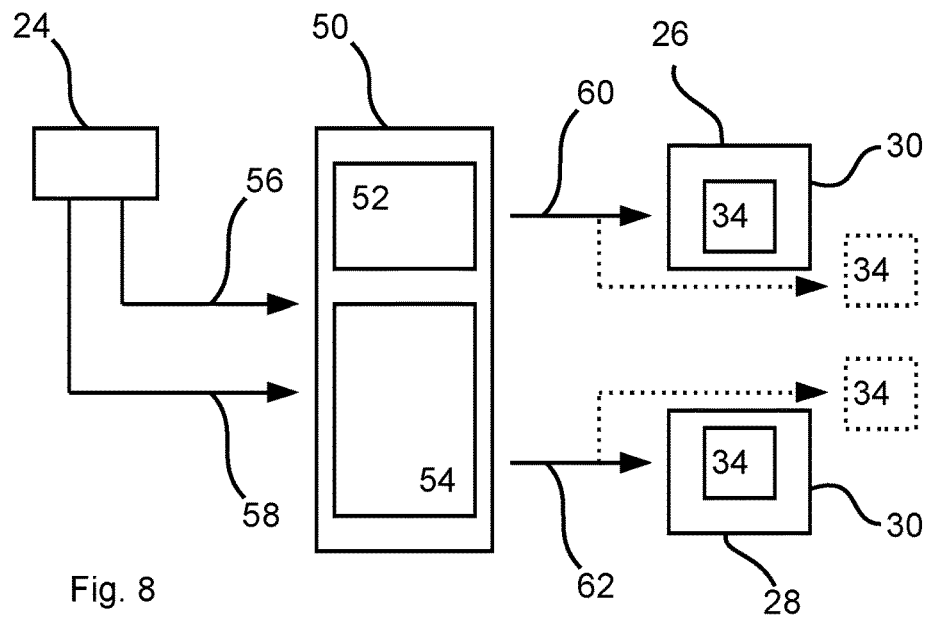
FIG. 8 is a schematic view showing a control device for operating the patient module.

The view in FIG. 8 shows a control device 50, which is optionally either a part of the patient module 20, but it may just as well be separated in space from the patient module 20 and may be carried, for example, by the patient himself. As an alternative, it is also possible that the control device 50 is associated with the pressure source 12, i.e., it is, for example, a part of a ventilator or the like, which acts as a pressure source 12. The control device 50 comprises, in a manner basically known per se, a processing unit 52 in the form of or in the manner of a microprocessor as well as a memory, into which a computer program acting as a control program 54 is loaded.

The computer program determines the essential functionality of the patient module 20. It is shown in this connection for illustration in FIG. 8 that sensor signals 56, 58, which can be obtained from the sensor mechanism 24, can be generated by means of the control device 50 and under the control of the control program 54 for obtaining at least one control signal 60, 62 for actuating the at least one valve 28 (exhalation valve 28) or of the valves 26, 28 (inhalation valve 26, exhalation valve 28), namely for actuating the respective valve drive 34, and are generated during the operation of the patient module 20. The control device 50 processes as a sensor signal 56, 58 or sensor signals 56, 58, for example, a first sensor signal 56 coding a pressure measured value and/or a second sensor signal 58 coding a flow measured value. The determination of the at least one control signal 60, 62 is carried out in a manner basically known per se to obtain a preset or presettable pressure and/or volume flow curve during the ventilation of the patient with phases of inhalation and exhalation following each other cyclically.

In case of a control device 50 not arranged in the patient module 20, the sensor signal or sensor signals 56, 58 is/are transmitted in a manner basically known per se in a wired or wireless manner to the control device 50 and the at least one control signal 60, 62 is transmitted in a wired or wireless manner to the respective valve device 30 and to the valve drive 34 comprised by—in the case of an embodiment according to FIG. 6—to the respective valve drive 34. The removal of the control device 50 from the patient module 20 has the advantage that the control device 50 is preserved in case of a possibly necessary disposal of the patient module 20 and can be used again with another patient module 20. If the valve drive 34 is separated in space from the respective valve device 30 (FIG. 6), this also applies to the valve drive 34 or to each valve drive 34.

The determination of the control signals 60, 62 and a respective pressure and/or volume flow curve during the phases of inhalation and exhalation is not a key aspect in the innovation being presented here, so that reference can thus be made to the state of the art. The peculiar feature here is that, on the one hand, the sensor mechanism 24 is arranged in the patient module 20 or at any rate close to the patient module 20 and that, on the other hand, the valves 26, 28 are likewise arranged in the patient module 20. Measured values, especially pressure and/or flow measured values, which represent the actual conditions in the patient's lungs 10 especially well, can be recorded by means of the sensor mechanism 24 in the patient module 20 or close to the patient module 20, i.e., at any rate close to the patient. Unlike in the case of a sensor mechanism located, for example, in the ventilator, the measured values, which can be recorded by means of the sensor mechanism 24 in the patient module 20 or close to the patient module 20 and are recorded during the operation, are not distorted by run time effects along the tube system (inhalation tube 16 and/or exhalation tube 18) between the ventilator and the patient interface 14. An especially accurate control or regulation of the pressure and/or volume flow curve is possible in this manner during the phases of inhalation and exhalation.

The patient module 20 is integrated in the path of the breathing gas in a modular form between the pressure source 12 and the patient's lungs 10 or can be integrated in this breathing gas path. The patient module 20 has for this purpose at least one standardized connection point on an inlet side facing the pressure source 12 and likewise at least one standardized connection point on an outlet side facing the patient. An inhalation tube 16 or an inhalation tube 16 and an exhalation tube 18 are connected correspondingly to the patient module 20 preferably by means of standardized connection points in the form of connection points each, which are formed each by a so-called medical cone. The respective valve devices 30 or the at least one valve device 30 are connected to these connection points in a fluid-communicating manner in the interior of the patient module 20.

The patient interface 14 can preferably likewise be connected detachably to the patient module 20 by means of at least one such standardized connection point in the form of at least one medical cone acting as a connection point. A patient module 20 can be easily replaced by detaching the units connected to the respective connection points and be replaced by another patient module 20 as needed.

Figure 9:
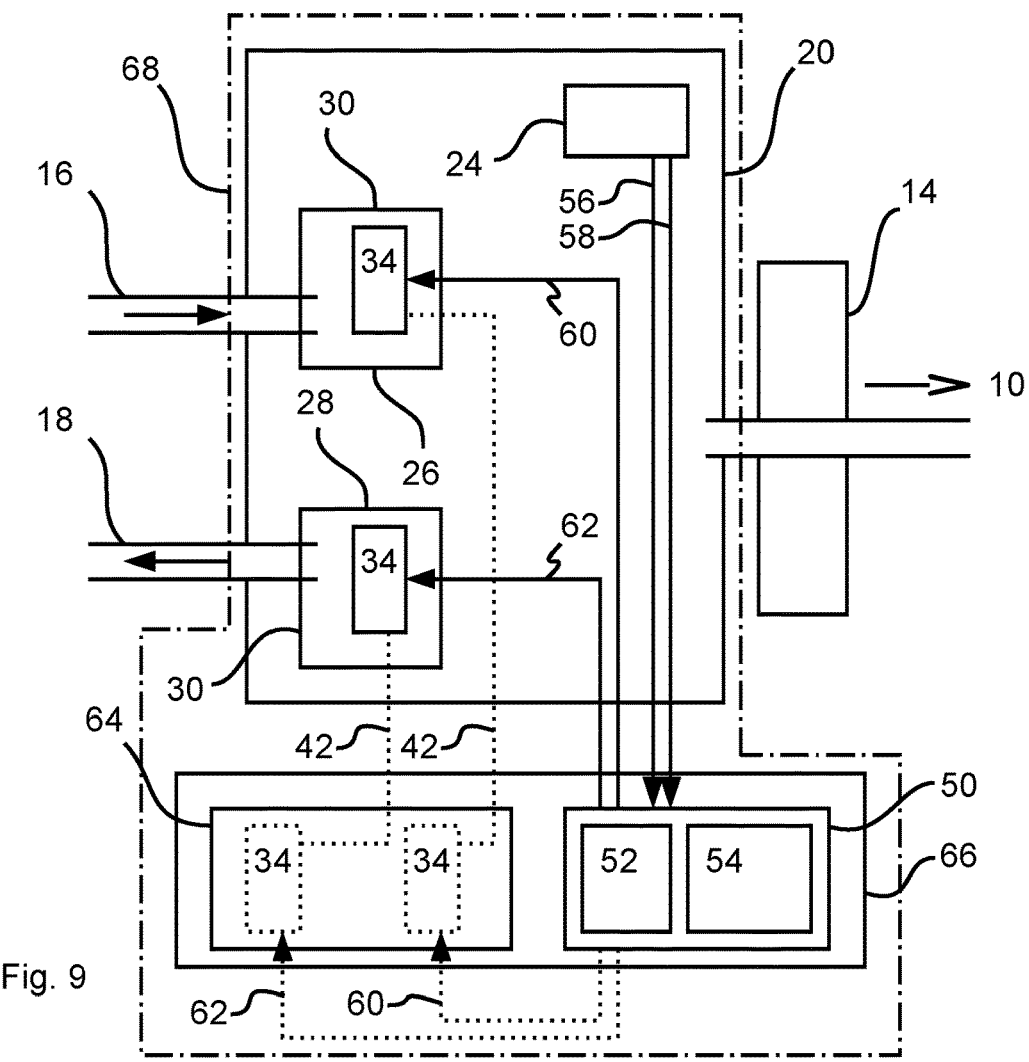
FIG. 9 is a schematic view showing the patient module according to FIG. 2 with an illustration of possible locations of valve drives in relation to the valve device or to each valve device comprised by the patient module.

The view in FIG. 9 shows the patient module 20 according to FIG. 2 with further details. A valve drive 34 is shown for each valve device 30 with a border drawn in solid lines as well as with a border drawn in broken lines. This shall illustrate that the valve drive 34 may be associated in space with the respective valve device 30 (border drawn in solid lines) or may even be arranged at a spaced location in space from the respective valve device 30 (border drawn in broken lines). Each valve drive 34 may be located in a housing of its own. The valve drive 34 forms now, together with its housing, a valve drive module 64. Two valve drives 34 separated in space from the patient module 20 may also be arranged together in one housing and likewise form a valve drive module 64.

All possible permutations may be considered, in principle, concerning the location of the valve drive 34 or each valve drive 34 for the patient module 20 being proposed here. It was already explained that the patient module 20 comprises at least one valve device 30, especially a valve device 30 acting as an exhalation valve 28. The valve drive 34 of this at least one valve device 30 may be located inside the patient module 20 or at a spaced location in space from the patient module 20 outside the patient module 20, for example, in a valve drive module 64. In case of at least two valve devices 30 comprised by the patient module 20, each valve drive 34 of the at least two valve devices 30 may be located inside or outside the patient module 20. In case of each valve drive 34 located outside the patient module 20, especially in case of a valve drive 34 arranged outside the patient module 20 in a housing of a valve drive module 64, this [valve drive] is connected pneumatically to the part of the respective valve device 30 that is located in the patient module 20, especially in a manner as this was explained above in connection with the explanation of the view shown in FIG. 6.

In case of an external valve drive 34 of the at least one valve device 30 (exhalation valve 28) or external drives 34 of the inhalation valve 26 and/or of the exhalation valve 28, the valve drive 34 or each valve drive 34 can preferably also be connected detachably to the patient module 20 and is detachably connected to this during the operation of the patient module 20. The connection is in the form of the tube 36 (FIG. 6). Wires (electrical connection lines), not shown, for applying an electrical voltage to the piezo element 118 (FIG. 4) of the valve drive, run either likewise to the patient module 20 or to another unit, for example, the control device 50.

To separate a valve drive 34 from the patient module 20, the tube 36 and optionally these wires are detached. The wires are led, for example, to a plug, which can be plugged in the interior of the patient module 20 (or alternatively in the interior of a control device 50 separated in space from the patient module 20) into a connection jack provided there. The wires can thus be connected detachably to the patient module 20 and/or to the valve drive module 64. The tube 36 to the valve drive 34 is connected detachably to the valve drive 34 at at least one connection point and is thus likewise connected as a whole detachably to the patient module 20. By detaching the wires and the tube 36, each valve drive 34 can be separated from the patient module 20. The wires and the tube 36 may be led to a common plug and to a connection jack fitting same.

The statements made above in reference to the wires leading to each valve drive 34 apply correspondingly to an external control device 50 with wires for the wired transmission of the at least one sensor signal 56, 58 and of the at least one control signal 60, 62. Provisions are made here as well for the detachable connection of the control device 50 to the patient module 20 for the corresponding wires to be led at least on one side to a plug or the like, which can be plugged into a corresponding connection jack in the patient module 20 or on the side of the control device 50. By detaching the wires, a control device 50 separated in space from the patient module 20 can be separated from the patient module 20.

In case of a control device 50 separated in space from the patient module 20 as well as in case of at least one valve drive 34 separated in space from the patient module 20, the control device 50 as well as the valve drive 34 or each valve drive 34, especially in the form of a valve drive module 64 comprising the valve drive 34 or each valve drive 34, may be combined in a device part hereinafter called 66. This may be worn by the patient, for example, around the neck. In case of a necessary disposal of the patient module 20, the control module 66 is preserved and can be used further. In case of a necessary replacement of the patient module 20, for example, for cleaning purposes, the patient module 20 to be replaced can be replaced with a new patient module 20 or with a processed patient module 20 rapidly and without complications.

On the whole, a patient module system 68 is obtained. The extent of the patient module system 68 depends on the location of the at least one valve drive 34 or of the valve drives 34 and/or on the location of the control device 50. Accordingly, the patient module system 68 comprises at least the patient module 20. Depending on the configuration, the patient module system 68 comprises an external valve drive 34 or two external valve drives 34, the valve drive 34 or each valve drive 34 being able to be arranged in a valve drive module 64 and the patient module system 68 will thus also comprise such a valve drive module 64. Further, the patient module system 68 possibly comprises an external control device 50. If the external control device 50 and the external valve drive 34 or each external valve drive 34 or a valve drive module 64 comprising an external valve drive 34 or each external valve drive 34 is combined into a control module 66, the patient module system 68 also comprises such a control module 66.

Individual key aspects of the description submitted here can thus be briefly summarized as follows. Proposed is a device intended for use together with a pressure source 12 and called a patient module 20 here for ventilating a patient. This [device] is characterized in that it couples the pressure source 12 for flow to a patient interface 14, which can be connected to the airways of a patient, and that it comprises at least one valve device 30, which can be controlled by means of a piezo pump, which acts as a valve drive 34 and can preferably be operated at a high frequency, and wherein the at least one valve device 30 acts as an exhalation valve 28.

While specific embodiments of the invention have been shown and described in detail to illustrate the application of the principles of the invention, it will be understood that the invention may be embodied otherwise without departing from such principles.

The invention claimed is:

1. A patient module for use together with a pressure source, the patient module comprising:
   a pressure source coupling to couple the patient module to the pressure source for flow to a patient interface, which is configured to be connected to the airways of a patient;
   a patient interface connection whereby the patient module is detachably connected to the patient interface;
   at least one valve device acting as an exhalation valve, wherein the valve device comprises a diaphragm element having a closing element, a valve drive, a pressure chamber and a control pressure chamber and the valve drive is fluid communicatingly connected to the control pressure chamber for generating a control pressure in the control pressure chamber, wherein the control pressure chamber is separated from the pressure chamber by means of the diaphragm element having the closing element, wherein a first opening of the pressure chamber configured to be opened and closed by means of the closing element and the closing element is configured to be controlled via the diaphragm element by means of the control pressure, and wherein a piezo pump acts as the valve drive; and at least one additional valve device to provide at least two valve devices with respective valve drives, which is configured to be arranged inside or outside the patient module, and wherein one of the at least two valve devices acts as an exhalation valve and one of the at least two valve devices acts as an inhalation valve, wherein in the valve device acting as an inhalation valve, a branch line element connects to a connection chamber by exactly one connection line element communicatingly opening in the pressure chamber, the connection chamber being located outside of the connection line element, the valve drive being arranged such that the valve drive pumps gas from the connection chamber into the control pressure chamber and that it carries out a gas feed from the connection chamber into the control pressure chamber such that it brings about an increase in pressure in the control pressure chamber, at least a portion of the valve drive being located in the connection chamber.

2. A patient module in accordance with claim 1,
wherein each valve drive comprises a piezo element, to which an electrical voltage is configured to be applied, and
wherein a pump diaphragm element of each valve drive is configured to be moved by a voltage-dependent change in the deformation of the piezo element.

3. A patient module in accordance with claim 1, wherein each valve drive is fluid communicatingly connected or is configured to be fluid communicatingly connected inside or outside the patient module to a respective valve device.

4. A patient module in accordance with claim 1, wherein each valve device further comprises at least two connection line elements opening in the pressure chamber, and wherein the patient interface is configured to be connected to one of the at least two connection line elements opening in the pressure chamber, and the pressure source is configured to be connected to the other connection line element.

5. A patient module in accordance with claim 1, wherein the pressure source coupling is configured for detachable connection to at least one ventilation tube coming from the pressure source.

6. A patient module system comprising:
a patient module comprising a pressure source coupling to couple the patient module to a pressure source for flow to a patient interface, which is configured to be connected to the airways of a patient, a patient interface connection, whereby the patient module is detachably connected to the patient interface; at least one valve device acting as an exhalation valve, wherein the valve device comprises a diaphragm element having a closing element, a valve drive, a pressure chamber and a control pressure chamber and the valve drive is fluid communicatingly connected to the control pressure chamber for generating a control pressure in the control pressure chamber, wherein the control pressure chamber is separated from the pressure chamber by means of the diaphragm element having the closing element, wherein a first opening of the pressure chamber is configured to be opened and closed by means of the closing element and the closing element is configured to be controlled via the diaphragm element by means of the control pressure, and wherein a piezo pump acts as the valve drive, and a sensor mechanism, the patient module further comprising at least one additional valve device to provide at least two valve devices with respective valve drives, which is configured to be arranged inside or outside the patient module, and wherein one of the at least two valve devices acts as an exhalation valve and one of the at least two valve devices acts as an inhalation valve, wherein a branch line element connects in the valve device acting as an inhalation valve a connection chamber to exactly one connection line element fluid communicatingly opening in the pressure chamber, the connection chamber being outside of the branch line element, the valve drive being arranged such that the valve drive pumps gas from the connection chamber into the control pressure chamber and that it carries out a gas feed from the connection chamber into the control pressure chamber such that it brings about an increase in pressure in the control pressure chamber, at least a portion of the valve drive being located in the connection chamber;
a control device, which is configured to be arranged inside or outside the patient module, wherein at least one control signal can be generated by means of the control device on the basis of at least one sensor signal that is configured to be obtained from the sensor mechanism for actuating at least one valve device of the patient module.

7. A patient module system in accordance with claim 6, wherein the control device is separated in space from the patient module and is signal connected to the patient module for obtaining the at least one sensor signal from the sensor mechanism as well as for transmitting the at least one control signal to at least one valve device of the patient module.

8. A patient module system comprising:
a pressure source; and
a patient module comprising a pressure source coupling to couple the patient module to a pressure source for flow to a patient interface, which is configured to be connected to the airways of a patient, a patient interface connection, whereby the patient module is detachably connected to the patient interface; at least one valve device acting as an exhalation valve, wherein the valve device comprises a diaphragm element having a closing element, a valve drive, a pressure chamber and a control pressure chamber and the valve drive is fluid communicatingly connected to the control pressure chamber for generating a control pressure in the control pressure chamber, wherein the control pressure chamber is separated from the pressure chamber by means of the diaphragm element having the closing element, wherein a first opening of the pressure chamber is configured to be opened and closed by means of the closing element and the closing element is configured to be controlled via the diaphragm element by means of the control pressure, and wherein a piezo pump acts as the valve drive, wherein a ventilator acts as the pressure source and the ventilator acts as an operating and user interface for the patient module, the patient module further comprising at least one additional valve device to provide at least two valve devices with respective valve drives, which is configured to be arranged inside or outside the patient module, and wherein one of the at least two valve devices acts as an exhalation valve and one of the at least two valve devices acts as an inhalation valve, wherein a branch line element connects in the valve device acting as an inhalation valve a connection chamber to exactly one connection line element fluid communicatingly opening in the pressure chamber, the connection chamber being located outside of the branch line element, the valve drive being arranged such that the valve drive pumps gas from the connection chamber into the control pressure chamber and that it carries out a gas feed from the connection chamber into the control pressure chamber such that it brings about an increase in pressure in the control pressure chamber, at least a portion of the valve drive being located in the connection chamber.

9. A patient module system according to claim 8, wherein the ventilator has a control device and acts as an operating and user interface for the patient module.

10. A patient module system comprising:
a pressure source;
a patient module comprising a pressure source coupling to couple the patient module to a pressure source for flow to a patient interface, which is configured to be connected to the airways of a patient, a patient interface connection, whereby the patient module is detachably connected to the patient interface; at least one valve device acting as an exhalation valve, wherein the valve device comprises a diaphragm element having a closing element, a valve drive, a pressure chamber and a control pressure chamber and the valve drive is fluid communicatingly connected to the control pressure chamber for generating a control pressure in the control pressure chamber, wherein the control pressure chamber is separated from the pressure chamber by means of the diaphragm element having the closing element, wherein a first opening of the pressure chamber is configured to be opened and closed by means of the closing element and the closing element is configured to be controlled via the diaphragm element by means of the control pressure, and wherein a piezo pump acts as the valve drive, and a sensor mechanism, the patient module further comprising at least one additional valve device to provide at least two valve devices with respective valve drives, which is configured to be arranged inside or outside the patient module, and wherein one of the at least two valve devices acts as an exhalation valve and one of the at least two valve devices acts as an inhalation valve, wherein a branch line element connects in the valve device acting as an inhalation valve a connection chamber to exactly one connection line element fluid communicatingly opening in the pressure chamber, the connection chamber being located outside of the branch line element, the valve drive being arranged such that the valve drive pumps gas from the connection chamber into the control pressure chamber and that it carries out a gas feed from the connection chamber into the control pressure chamber such that it brings about an increase in pressure in the control pressure chamber, wherein at least a portion of the valve drive is located in the connection chamber; and
a control device, which is configured to be arranged inside or outside the patient module, wherein at least one control signal is generated by means of the control device based on at least one sensor signal that is configured to be obtained from the sensor mechanism for actuating at least one valve device of the patient module, wherein a constant pressure source acts as the pressure source and the control device acts as an operating and user interface for the patient module.

11. A patient module system according to claim 8, further comprising a control device, which is configured to be arranged inside or outside the patient module, wherein:
the patient module further comprises a sensor mechanism; and
at least one control signal is generated by means of the control device based on at least one sensor signal that is configured to be obtained from the sensor mechanism for actuating at least one valve device of the patient module.

12. A patient module system according to claim 8, wherein the connection chamber is located at a spaced location from the pressure chamber and the control pressure chamber.

13. A patient module system according to claim 8, wherein the branch line element comprises a branch line element outlet, wherein the connection chamber is configured to receive fluid via the branch line element outlet, the connection chamber being located between the branch line element outlet and the valve drive.

14. A patient module system according to claim 8, wherein the piezo pump is located at a position outside of the pressure chamber and the control pressure chamber, the diaphragm element being located at a position outside of the connection chamber.

15. A patient module in accordance with claim 1, wherein the connection chamber is located at a spaced location from the pressure chamber and the control pressure chamber, the at least one valve device comprising a valve device housing, the valve device housing comprising a valve device housing inner surface, the valve device housing inner surface defining at least a portion of the connection chamber.

16. A patient module in accordance with claim 1, wherein the at least one valve device comprises a valve device housing, the valve device housing comprising a valve device housing inner surface, the valve device housing inner surface defining at least a portion of the connection chamber.

17. A patient module in accordance with claim 1, wherein the piezo pump is located at a position outside of the pressure chamber and the control pressure chamber, the diaphragm element being located at a position outside of the connection chamber.

18. A patient module system in accordance with claim 10, wherein the connection chamber is located at a spaced location from the pressure chamber and the control pressure chamber, the at least one valve device comprising a valve device housing, the valve device housing comprising a valve device housing inner surface, the valve device housing inner surface defining at least a portion of the connection chamber.

19. A patient module system in accordance with claim 10, wherein the piezo pump is located at a position outside of the pressure chamber and the control pressure chamber, the diaphragm element being located a position outside of the connection chamber.

* * * * *